United States Patent [19]

Watanabe et al.

[11] Patent Number: 4,985,125
[45] Date of Patent: Jan. 15, 1991

[54] METHOD FOR DETECTING MEAT FRESHNESS USING A BIOSENSOR

[75] Inventors: Etsuo Watanabe, Kanagawa; Masakazu Hoshi, Tokyo, both of Japan

[73] Assignee: Taiyo Fishery Co., Ltd., Tokyo, Japan

[21] Appl. No.: 449,245

[22] Filed: Dec. 7, 1989

Related U.S. Application Data

[62] Division of Ser. No. 289,552, Dec. 22, 1988, abandoned.

[30] Foreign Application Priority Data

Jan. 8, 1988 [JP] Japan .................................... 63-2021

[51] Int. Cl.[5] .................... G01N 27/40; G01N 27/327
[52] U.S. Cl. ......................... 204/153.12; 204/153.17; 204/153.2; 204/403; 204/415; 435/817; 436/806
[58] Field of Search ........... 204/403, 409, 415, 153.12, 204/153.17, 153.2; 435/817; 436/806

[56] References Cited

U.S. PATENT DOCUMENTS

| 4,467,811 | 8/1984 | Clark | 204/403 |
| 4,483,924 | 11/1984 | Tsuji et al. | 204/403 |
| 4,490,234 | 12/1984 | Buzza | 204/409 |
| 4,525,265 | 6/1985 | Abe et al. | 204/403 |
| 4,533,456 | 8/1985 | Kratochvil et al. | 204/415 |
| 4,544,455 | 10/1985 | Eisenhardt et al. | 204/403 |
| 4,627,893 | 12/1986 | Cormier et al. | 204/402 |

Primary Examiner—T. Tung
Attorney, Agent, or Firm—Frishauf, Holtz, Goodman & Woodward

[57] ABSTRACT

A biosensor comprising a main body and a built-in sensing electrode provided therein, wherein said sensing electrode is provided with a sensing part to which a buffer solution can be constantly fed and said main body is provided with an inlet which is brought into direct contact with a specimen to thereby incorporate the molecule to be assayed from said specimen therethrough, said inlet being covered with a membrane through which the molecule to be assayed can permeate. This biosensor enables a specified molecule contained in a specimen to be rapidly and conveniently assayed without requiring any pretreatment of the specimen.

4 Claims, 8 Drawing Sheets

METHOD FOR DETECTING MEAT FRESHNESS USING A BIOSENSOR

This application is a division of application Ser. No. 289,552, filed Dec. 22, 1988, now abandoned.

BACKGROUND OF THE INVENTION

1. Field of the Invention:

This invention relates to a biosensor. More particularly, it relates to a biosensor wherein the unique properties of an enzyme or a microorganism are utilized.

2. Description of the Prior Art:

The sensing part of a common biosensor basically consists of a substance capable of recognizing a specified molecule and an electrochemical device, i.e., a transducer converting the recognition information of said substance into an electrical signal.

Known biosensors of the abovementioned type may be classified into, for example, enzymatic biosensors and microbial ones depending on said substance capable of recognizing a specified molecule. Alternatively, they may be classified into, for example, glucose sensor, ethyl alcohol sensor, acetic acid sensor etc., depending on the molecule to be recognized. These biosensors enable a molecule to be assayed within a significantly short period of time as compared with conventional chemical assay methods such as colorimetry.

However these biosensors have a disadvantage. More particularly, a common assay with a biosensor comprises constantly feeding a specified buffer solution to the sensing part while introducing a specimen solution on an upstream side of the same, i.e., so-called flow injection assay. Although this assay per se can be completed within a short period of time of, e.g., ten minutes, a pretreatment for preparing the specimen solution takes a prolonged period of time of, e.g., 10 to 30 minutes.

SUMMARY OF THE INVENTION

It is an object of the present invention to provide a biosensor by which a specified molecule contained in a specimen can be rapidly and readily assayed without requiring any particular pretreatment for preparing a specimen solution.

As the result of extensive studies, the present inventors have found that the above object can be achieved by providing a biosensor comprising a main body having a built-in sensing electrode with an inlet covered with a specified membrane and bringing said inlet into contact with a specimen under specified conditions to thereby directly assay the aimed molecule contained in said specimen.

Accordingly the present invention has been completed based on the above finding and provides the following biosensors.

A biosensor of an integral structure comprising a main body having a built-in sensing electrode: wherein a buffer solution can be constantly fed to the sensing part of said sensing electrode; said main body is provided with an inlet to be in contact with a specimen, through which the molecule to be assayed may be introduced; and said inlet is covered with a membrane through which the molecule to be assayed can permeate.

A biosensor of a separatory structure comprising a main body having a built-in sensing electrode: wherein a buffer solution can be constantly fed to the sensing part of said sensing electrode; said main body is connected to a contact zone via said buffer solution; said contact zone is provided with an inlet to be in contact with a specimen, through which the molecule to be assayed may be introduced; and said inlet is covered with a membrane through which the molecule to be assayed can permeate. Function:

The biosensor as defined above enables a specified molecule contained in a specimen to be directly assayed, since the molecule to be assayed can be directly introduced from the specimen to the main body via the inlet. Further the assay can be more readily and conveniently effected by locating said inlet at the contact part separated from the main body.

DETAILED DESCRIPTION OF THE INVENTION

Now an embodiment of the biosensor of the present invention will be described by referring to FIGS. 1 and 2.

Figure 1:
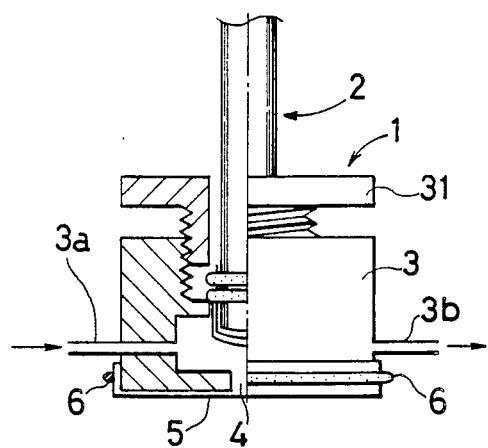
FIG. 1 is a partial sectional view of an embodiment of the biosensor of the present invention
Figure 2:
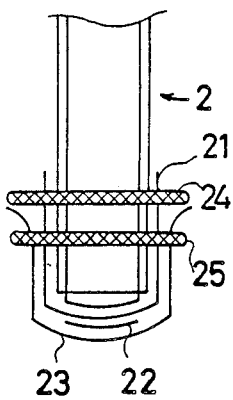
FIG. 2 is a schematic view of a built-in sensing electrode provided in the abovementioned sensor.

FIG. 1 is a partial sectional view which schematically shows an embodiment of the biosensor of the present invention, while FIG. 2 is a schematic view of a built-in sensing electrode provided therein.

The biosensor 1 shown in FIG. 1 consists of a main body 3 having a built-in sensing electrode 2 therein. An inlet 3a and an outlet 3b, each for a buffer solution are provided at the lower part of said main body 3 so as to enable constant feed of the buffer solution to the tip of the abovementioned sensing electrode 2.

Further the main body 3 is provided with another inlet 4 which is in contact with a specimen (not shown in FIG. 1) to thereby introduce the molecule to be assayed into the main body 3 there through. This inlet 4 is covered with a membrane 5 through which the molecule to be assayed can permeate. In FIG. 1, this membrane 5 is attached around the lower part of the main body 3 with an O-ring 6.

Any membrane may be employed as the membrane 5 without limitation so long as the molecule to be assayed can permeate therethrough. For example, a dialysis membrane, a membrane filter or an ultrafiltration membrane may be used therefor.

The sensing part of the abovementioned sensing electrode 2 comprises, for example, a substance capable of recognizing a specified molecule, such as an immobilized enzyme or an immobilized microorganism, fitted in the tip (electrode) of an oxygen electrode or a pH electrode. The fitting of, for example, the abovementioned immobilized enzyme may be arbitrarily carried out without particular restriction. For example, as shown in FIG. 2, the sensing electrode may be successively covered with a Teflon membrane 21 and an immobilized enzyme (membrane) 22 and finally with a dialysis membrane 23. These Teflon membrane 21 and dailysis membrane 23 are fixed around the sensing electrode 2 respectively with 0-rings 24 and 25.

The abovementioned sensing electrode 2 is inserted into the main body 3 from above and fixed with a fixing member 31 screwed on the top of the main body 3.

Now the function of the biosensor of the present invention will be illustrated by referring to Example 3, by citing a biosensor wherein a sensing electrode is an enzyme electrode whose sensing part comprises an oxygen electrode and immobilized glucose oxidase as an example.

Figure 3:
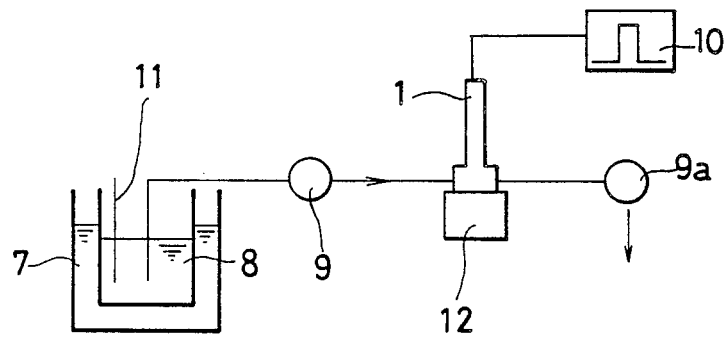
FIG. 3 is a flow sheet roughly showing an assay system including the biosensor.

FIG. 3 schematically shows a sensor system involving the biosensor 1 of the present embodiment. This sensor system comprises: an oxygen-saturated buffer solution 8 which is immersed in a thermostat 7 and thus maintained at a constant temperature; a pump 9 for feeding said buffer solution 8 to the abovementioned biosensor 1; another pump 9a for removing said solution 8 outside the system from said biosensor 1; and a recorder 10 for recording the electrical response of the biosensor 1. In addition, an air inlet 11 for blowing air into the buffer solution 8 in order to give a stabilized electrical response and to maintain the oxygen dissolved in the buffer solution 8 in a saturated state is further provided.

The buffer solution 8 maintained in a stable state is fed to the biosensor 1 under given conditions at a given rate to thereby determine the normal state for the assay. This is given as a stable base line by the recorder 10.

Subsequently the inlet 4 covered with a membrane 5 of the biosensor 1 is brought into contact with a specimen 12 and this state is maintained for a given period of time. During this period, the electrical response is recorded with the recorder 10.

The amount of the specified molecule to be assayed by the biosensor of this embodiment is expressed by the magnitude of the electrical signal such as current. This signal is recorded by the recorder 10. Accordingly, the amount of the specified molecule is determined from the height or area of a peak recorded by the recorder 10.

When the inlet 4 comes in contact with the specimen as described above, the molecule to be assayed is introduced from the specimen 12 into the main body 3 via the membrane 5 and then fed to the tip of the sensing electrode 2 of the biosensor 1. Namely, when glucose, which is to be assayed, contained in the specimen is fed to the abovementioned sensing part, oxygen is consumed according to the reaction formula (1), which lowers the amount of oxygen dissolved in the buffer solution in the main body 3. Thus it is possible to detect this change by the oxygen electrode corresponding to the sensing electrode 2 and to record the same with the recorder 10.

$$\text{glucose} + \text{oxygen} \rightarrow \text{gluconolactone} + \text{hydrogen peroxide} \tag{1}$$

In the sensor system of FIG. 3, the response of the biosensor 1, that is, the height or area of a peak recorded by the recorder 10 would increase with an increase in the glucose content of the specimen. Therefore, the amount of the glucose contained in the specimen can be determined therefrom.

As described above, the biosensor 1 of the present invention enables a specified molecule contained in the specimen 12, i.e., glucose to be rapidly, conveniently and directly assayed without requiring any pretreatment of the specimen 12, namely breaking the same.

Although the present invention has been described by reference to the above embodiment, the biosensor of the present invention is not restricted thereby.

Figure 4:
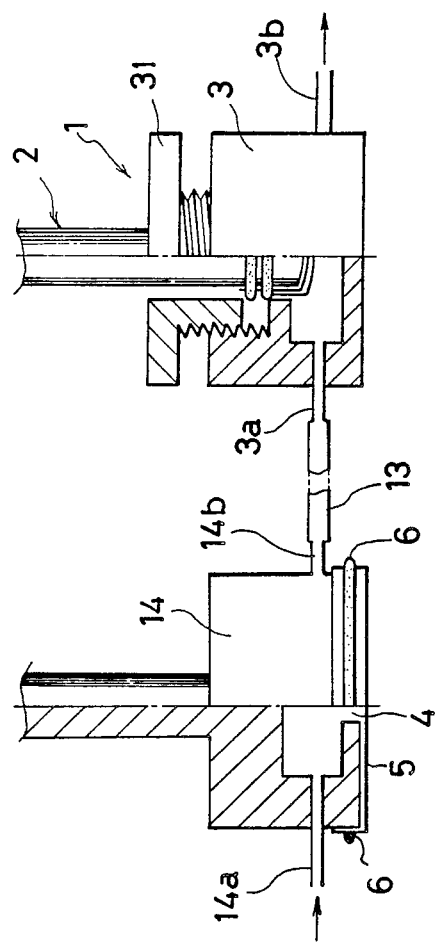
FIG. 4 is a partial sectional view of a biosensor of another embodiment.

For example, the biosensor of the present invention may comprise a main body, which is substantially the same as the one employed in the above embodiment but provided with no inlet, and a contact part 14 which is connected to the main body 3 and provided with an inlet 4 (cf. FIG. 4). The contact part 14 is connected to the main body 3 via a pipe for feeding the buffer solution to the main body 3. Namely, the contact part 14 and the main body 3 are connected to each other via the buffer solution. Thus, when the biosensor 1 of FIG. 4 is to be applied to the assay system of FIG. 3, said sensor is incorporated in such a manner that the oxygen-saturated buffer solution 8 is fed to the contact part 14 from an inlet 14a, then to the main body 3 via an outlet 14b, the pipe 13 and the inlet 3a of the main body, and finally discharged via the outlet 3b. The assay may be carried out in the same manner as the one described in the above embodiment by bringing the inlet 4 of the contact part 14 into direct contact with the specimen 12.

In the case of the biosensor of FIG. 4, the sample 12 can be further readily and conveniently assayed, since the inlet 4 for incorporating the molecule to be assayed from the specimen is located in the contact part 14 separated from the main body 3.

In addition to the enzyme electrode as described in the above embodiment, various electrodes including microbial electrodes and enzyme immunoelectrodes are available in the biosensor of the present invention.

When an enzyme electrode is to be used as a sensing electrode, the following biosensors may be prepared depending on the enzyme to be used in the enzyme electrode, in addition to the glucose sensor described in the above embodiment: sucrose sensor, maltose sensor, galactose sensor, ethanol sensor, phenol sensor, catachol sensor, lactic acid sensor, pyruvic acid sensor, uric acid sensor, amino acid sensor, L-glutamine sensor, L-glutamic acid sensor, L-asparagine sensor, L-tyrosine sensor, L-lysine sensor, L-arginine sensor, L-phenylalanine sensor, L-methionine sensor, urea sensor, cholesterol sensor, neutral lipid sensor, phospholipid sensor, monoamine sensor, penicillin sensor, amygdalin sensor, creatinine sensor, phosphate ion sensor, nitrate ion sensor, nitrite ion sensor, sulfate ion sensor, mercury ion sensor, hydrogen peroxide sensor etc.

When a microbial electrode is to be used as the sensing electrode, the following biosensors may be prepared depending on the selected microorganism: glucose sensor, fermented sugar sensor, methanol sensor, ethanol sensor, acetic acid sensor, formic acid sensor, glutamic acid sensor, lysine sensor, glutamine sensor, arginine sensor, aspartic acid sensor, ammonia sensor, nystatin sensor, nicotinic acid sensor, vitamin $B_1$ sensor, cephalosporin sensor, BOD sensor, viable count sensor etc.

In the above embodiment, a biosensor comprising a glucose sensor has been described in detail by referring to FIG. 3. It is needless to say, however, that the conditions for an assay system may be appropriately selected depending on the sensing electrode of each biosensor.

For example, the buffer solution is not restricted to an oxygen-saturated one but any buffer solution suitable for each sensing electrode may be employed.

To further illustrate the biosensor of the present invention, the following Experimental Examples wherein specimens were assayed with the use of the biosensor of the present invention will be given.

EXPERIMENTAL EXAMPLE 1

A sensing electrode 2 comprising an enzyme electrode was formed by fitting an immobilized glucose oxidase membrane, i.e., an immobilized enzyme, at the tip of an oxygen electrode. By using the obtained enzyme electrode, a biosensor (glucose sensor) wherein a main body 3 was separated from a contact part 14, as shown in FIG. 4, was prepared. The biosensor was then incorporated into an assay system of FIG. 3 and specimens were assayed therewith.

The specimens were jellies differing in glucose concentration from each other. Each specimen had been prepared to have a known glucose concentration.

The assay was conducted under the following conditions:

| buffer solution: | |
|---|---|
| 0.05M phosphate buffer solution | pH 7.5 |
| temperature | 30° C. |
| flow rate | 1.05 ml/min |
| immobilized enzyme | 50 U |
| membrane covering the inlet: | membrane filter (pore size: 2 μm) |

Figure 5:
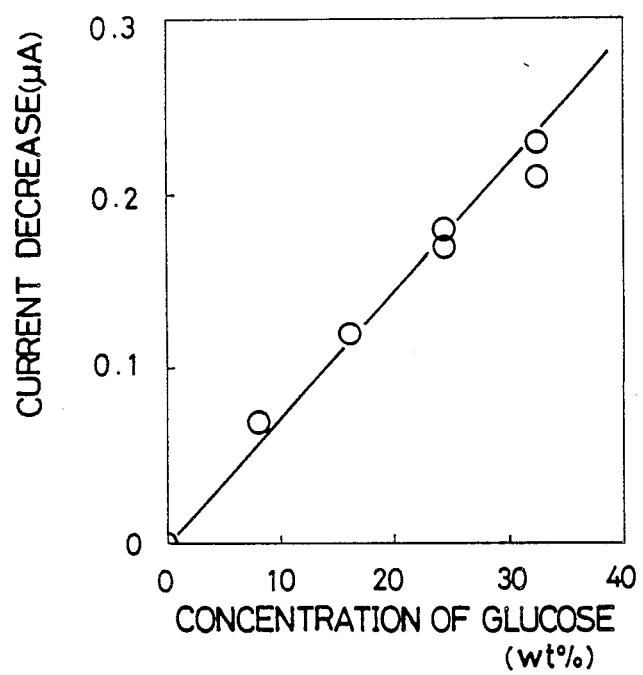
FIG. 5 is a graph showing the correlation between the glucose concentration of a specimen and the output of the biosensor.

FIG. 5 shows a graph wherein the ordinate refers to the current data (peak height) recorded by the recorder 10 while the abscissa refers to glucose concentration.

FIG. 5 obviously indicates that a definite correlation of a correlation coefficient of 0.996 is observed between the current data and glucose concentration.

EXPERIMENTAL EXAMPLE 2

A sensing electrode 2 comprising a microbial electrode was formed by fitting a membrane on which *Altermosas putrefaciens* was immobilized, i.e., an immobilized microorganism, at the tip of an oxygen electrode. By using the obtained microbial electrode, a biosensor 1 for detecting the freshness of fish meat, wherein a main body 3 was provided with an inlet 4 similar to the one of FIG. 1, was prepared. The abovementioned immobilized microorganism membrane was obtained by filtering a culture medium of said microorganism through a membrane filter and cutting the filter into a circle of 3 mm in diameter (cf. J. Food Sci., 52 (3), 592-595: Sensors for the Detection of Fish Freshness).

The obtained biosensor 1 was incorporated into an assay system of FIG. 3 and specimens were assayed therewith.

The specimens were commercially available tuna meat and beef meat. These samples were allowed to stand at room temperature and specified molecules such as free amino acids, fatty acids or sugars which would be formed through the metabolism of the microorganism with the lapse of time were monitored with the biosensor 1.

The assay was conducted under the following conditions:

| buffer solution: | |
|---|---|
| 0.1M phosphate buffer solution | pH 7.0 |
| temperature | 28° C. |
| flow rate | 0.5 ml/min |
| immobilized microorganism: | $5 \times 10^8$ cells/cm$^2$ |
| membrane covering the inlet: | membrane filter (pore size: 2 μm). |

Figure 6:
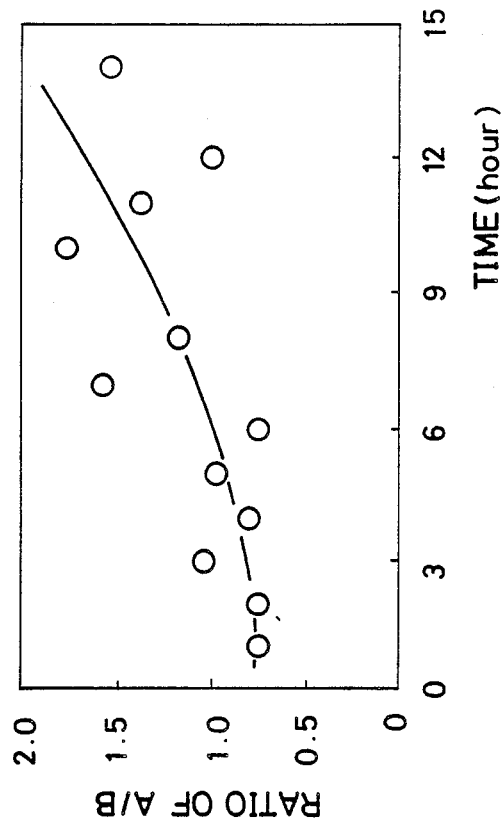
FIG. 6 is a graph showing the correlation between the change in fish meat with the lapse of time and the response of the sensor.
Figure 7:
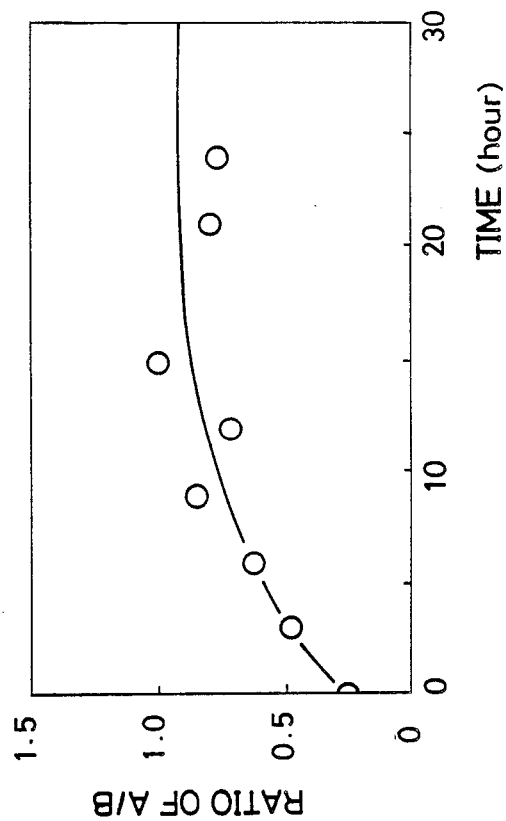
FIG. 7 is a graph showing the correlation between the change in beef meat with the lapse of time and the response of the sensor.

FIGS. 6 and 7 are graphs showing changes in the fish meat and beef meat, respectively, monitored with the biosensor 1. In each graph, the ordinate refers to the ratio A/B, wherein A represents the response of the sensor for the culture medium employed in the culture of *A. putrefaciens*, while B represents that for each specimen.

In the case of the tuna meat (FIG. 6), the ratio A/B showed little changes within four hours following the initiation of the assay and then showed a rapid increase. According to the result of an organoleptic test which was conducted simultaneously with the above assay, a putrefactive smell was noticed approximately after four hours, putrefaction was observed in appearance, smell and taste after five hours and the specimen became inedible after six hours unless cooked.

In the case of the beef meat (FIG. 7), on the other hand, the ratio A/B continuously increased within approximately ten hours following the initiation of the assay and then became stable. According to the result of an organoleptic test which was also conducted simultaneously with the assay, a putrefactive smell was noticed after nine hours and the specimen became inedible after 15 hours.

Thus the response of the sensor showed a large change in each case, when putrefaction was organoleptically noticed. This fact suggests that the response of the biosensor of the present invention shows an excellent correlation with freshness.

EXPERIMENTAL EXAMPLE 3

Figure 8:
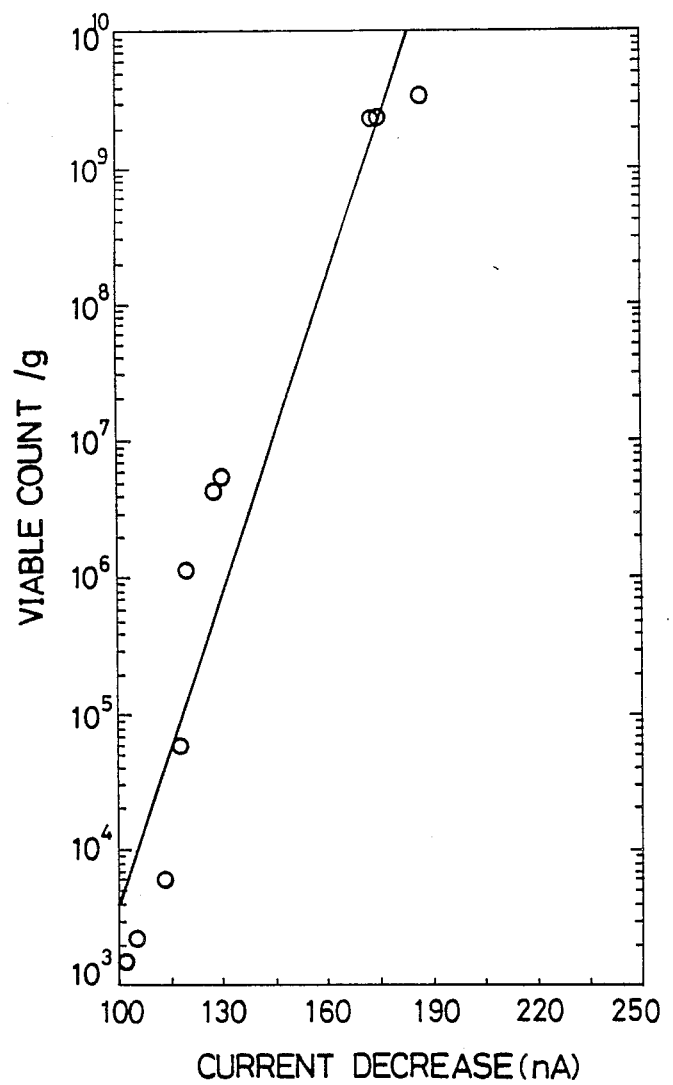
FIG. 8 is a graph showing the correlation between the viable count (Aerobic Plate Count. By Methods of Analysis of Association of the Official Agricultural Chemists) of pork meat and the output of the sensor.
Figure 9:
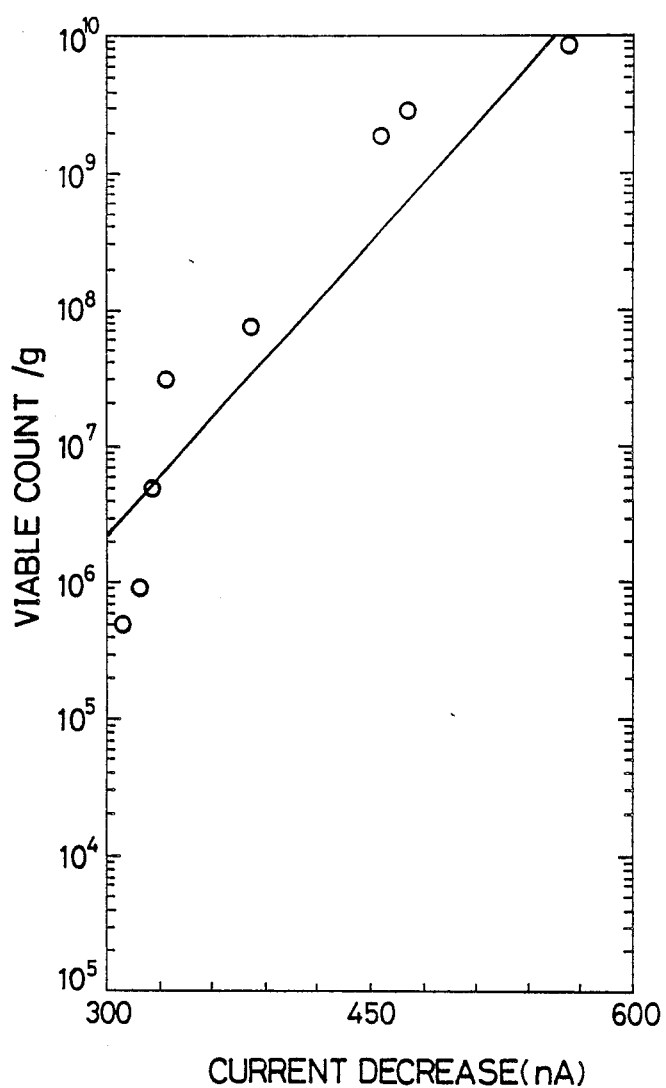
FIG. 9 is a graph showing the correlation between the viable count of chicken meat and the output of the sensor.
Figure 10:
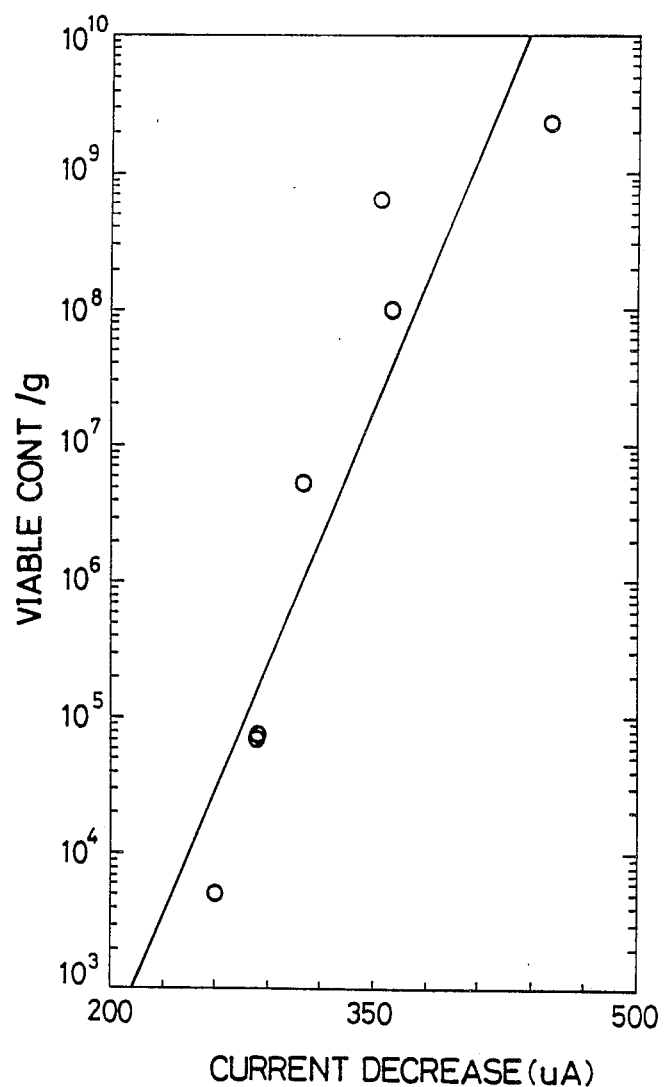
FIG. 10 is a graph showing the correlation between the viable count of tuna and the output of a sensor.

By using the same system as the one employed in the Experimental Example 2, pork meat, chicken meat and tuna meat, differing in viable count from each other, were assayed to thereby examine the relationship between the response of the biosensor of the present invention and viable count. FIGS. 8, 9 and 10 show the results.

These figures obviously indicate that an excellent correlation is observed between the response (output) of the sensor and the viable count of each specimen. This fact suggests that the biosensor of the present invention is useful.

What is claimed is:

1. A method for detecting freshness of meat comprising providing a biosensor comprising a main body and a built-in sensing electrode provided therein, said sensing electrode being provided with a sensing part, operable to generate a signal in response to a molecule to be assayed and to which a buffer solution can be constantly fed, and said main body being provided with an inlet which is brought into direct contact with a specimen to thereby incorporate the molecule to be assayed from said specimen therethrough, said inlet being covered with a membrane through which the molecule to be assayed can permeate, contacting the meat with the inlet of the biosensor, feeding the buffer solution to the sensor part, and measuring the signal generated by the sensing electrode; and correlating the signal with the degree of freshness of the meat.

2. The method of claim 1, wherein said sensing electrode is selected from the group consisting of an enzyme electrode, a microbial electrode and an enzyme immunoelectrode.

3. A method for detecting freshness of meat comprising providing a biosensor comprising a main body and a built-in sensing electrode provided therein, said sensing electrode being provided with a sensing part operable to generate a signal in response to a molecule to be assayed and to which a buffer solution can be constantly fed, and said main body being connected to a contact part via said buffer solution, said contact part being provided with an inlet which is brought into direct contact with a specimen to thereby incorporate the molecule to be assayed from said specimen therethrough, and said inlet being covered with a membrane through which the molecule to be assayed can permeate, contacting the meat with the inlet of the biosensor, feeding the buffer solution to the sensor part, and measuring the signal generated by the sensing electrode; and correlating the signal with the degree of freshness of the meat.

4. The method of claim 3, wherein said sensing electrode is selected from the group consisting of an enzyme electrode, a microbial electrode and an enzyme immunoelectrode.

* * * * *